United States Patent [19]

Conway et al.

[11] Patent Number: 5,137,671
[45] Date of Patent: Aug. 11, 1992

[54] METHODS OF MAKING BALLOON CATHETERS

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[21] Appl. No.: 462,832

[22] Filed: Jan. 10, 1990

[51] Int. Cl.$^5$ ............................................. B29C 67/18
[52] U.S. Cl. ................................... 264/130; 264/150; 264/254; 264/301; 264/305; 264/307
[58] Field of Search ............... 264/129, 130, 150, 250, 264/251, 259, 262, 263, 300, 301, 302, 305, 306, 307, 254

[56] References Cited

U.S. PATENT DOCUMENTS

| | | |
|---|---|---|
| 2,043,630 | 6/1936 | Raiche . |
| 2,230,226 | 4/1941 | Auzin . |
| 2,248,934 | 7/1941 | Auzin . |
| 2,308,484 | 1/1943 | Auzin et al. . |
| 2,314,262 | 3/1943 | Winder . |
| 2,322,858 | 6/1943 | Limbert et al. . |
| 2,330,399 | 9/1943 | Winder . |
| 2,330,400 | 9/1943 | Winder . |
| 2,390,070 | 12/1945 | Auzin . |
| 2,481,488 | 9/1949 | Auzin . |
| 2,690,595 | 10/1954 | Raiche . |
| 2,712,161 | 7/1955 | Moss . |
| 3,304,353 | 2/1967 | Harautuneian ........................ 264/130 |
| 3,394,705 | 7/1968 | Abramson . |
| 3,409,016 | 11/1968 | Foley . |
| 3,539,674 | 11/1970 | Dereniuk et al. .................... 264/306 |
| 3,544,668 | 12/1970 | Dereniuk ............................ 264/306 |
| 3,556,294 | 1/1971 | Walck, III et al. . |
| 3,606,889 | 9/1971 | Arblaster . |
| 3,683,928 | 8/1972 | Kuntz . |
| 3,695,921 | 10/1973 | Shepherd et al. . |
| 3,854,483 | 12/1974 | Powers . |
| 3,879,516 | 4/1975 | Wolvek . |
| 3,894,540 | 7/1975 | Bonner, Jr. . |
| 4,029,104 | 6/1977 | Kerber ................................ 128/348 |
| 4,062,363 | 12/1977 | Bonner, Jr. . |
| 4,133,303 | 1/1979 | Patel . |
| 4,149,539 | 4/1979 | Cianci . |
| 4,196,731 | 4/1980 | Laurin et al. . |
| 4,198,984 | 4/1980 | Taylor . |
| 4,265,848 | 5/1981 | Rüsch ................................ 264/130 |
| 4,269,310 | 5/1981 | Uson . |
| 4,284,459 | 8/1981 | Patel et al. ......................... 156/245 |
| 4,381,008 | 4/1983 | Thomas et al. . |
| 4,472,226 | 9/1984 | Redinger et al. . |
| 4,571,239 | 2/1986 | Heyman . |
| 4,571,240 | 2/1986 | Samson et al. . |
| 4,601,713 | 7/1986 | Fuqua . |
| 4,612,337 | 12/1986 | Fox, Jr. et al. . |
| 4,622,033 | 11/1986 | Taniguchi . |
| 4,627,844 | 12/1986 | Schmitt . |
| 4,634,433 | 1/1987 | Osborne . |
| 4,652,259 | 3/1987 | O'Neil . |
| 4,664,657 | 5/1987 | Williamitis et al. . |
| 4,687,470 | 8/1987 | Okada . |
| 4,710,181 | 12/1987 | Fuqua . |
| 4,737,219 | 4/1988 | Taller et al. . |
| 4,775,371 | 10/1988 | Mueller et al. . |

OTHER PUBLICATIONS

The Bard Hospital Division brochure (copyright on a date unknown prior to Nov. 9, 1989 by C. T. Bard, Inc., Murray Hill, NJ 07974).

Primary Examiner—Jan H. Silbaugh
Assistant Examiner—Brian J. Eastley
Attorney, Agent, or Firm—Merchant, Gould, Smith, Edell, Welter & Schmidt

[57] ABSTRACT

A method of making a balloon catheter. The method includes the steps of providing a tube having an outer surface and a plurality of lumens including first and second lumens, the tube including a first lumen access opening in the outer surface communicating with the first lumen; simultaneously coating a first portion of the outer surface with an amount of a bond preventing agent effective to prevent bonding to the first portion of the outer surface and plugging the first lumen access opening; and subsequently coating a second portion of the outer surface and the coating of bond preventing agent on the first portion of the outer surface with a polymeric bonding composition, wherein a resilient overcoat layer is created which is fixed to and integral with the tube proximate the second portion of the outer surface and free from adherence to the tube proximate the first portion of the outer surface. An alternate embodiment provides a method of mass-producing balloon catheters.

14 Claims, 5 Drawing Sheets

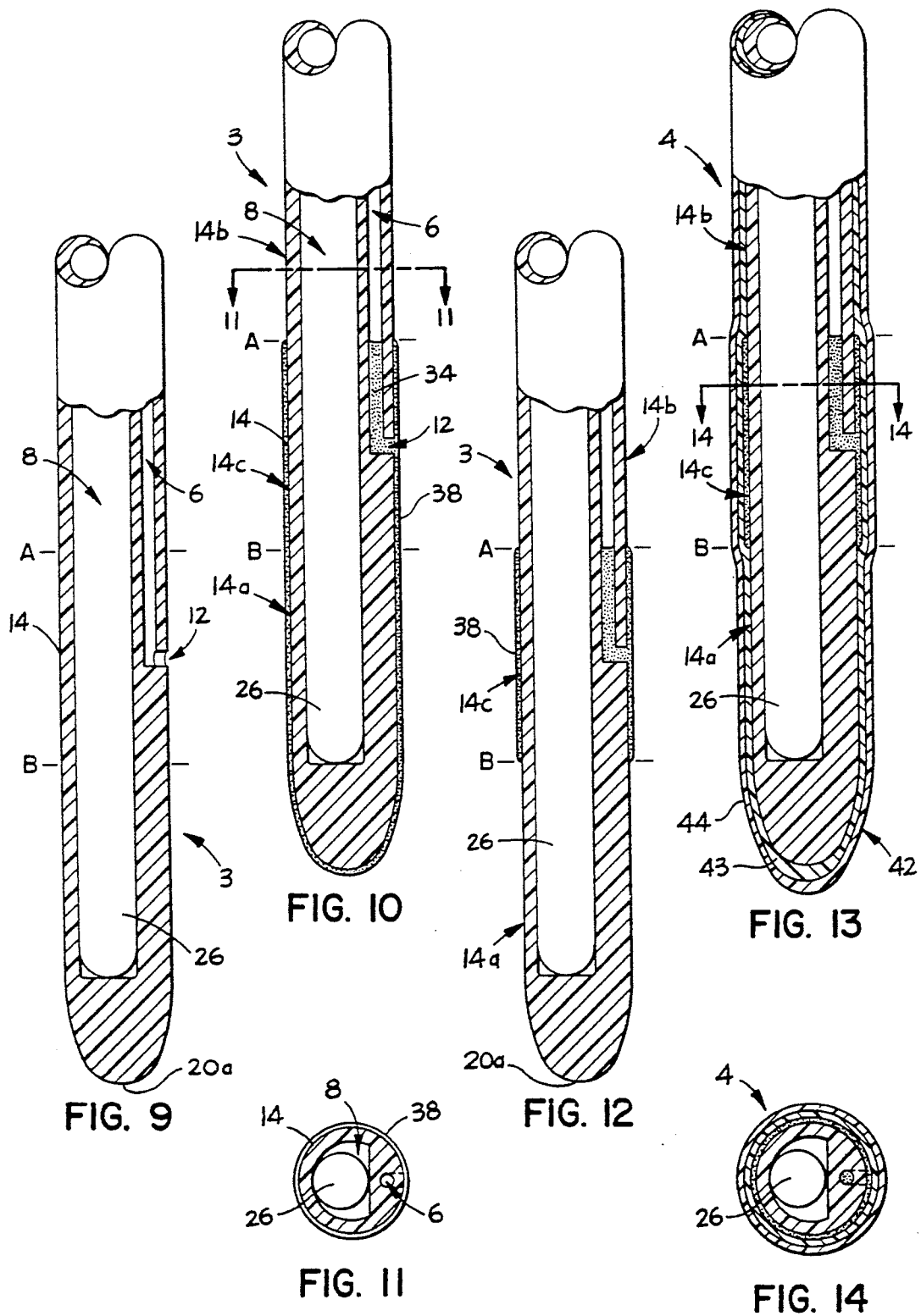

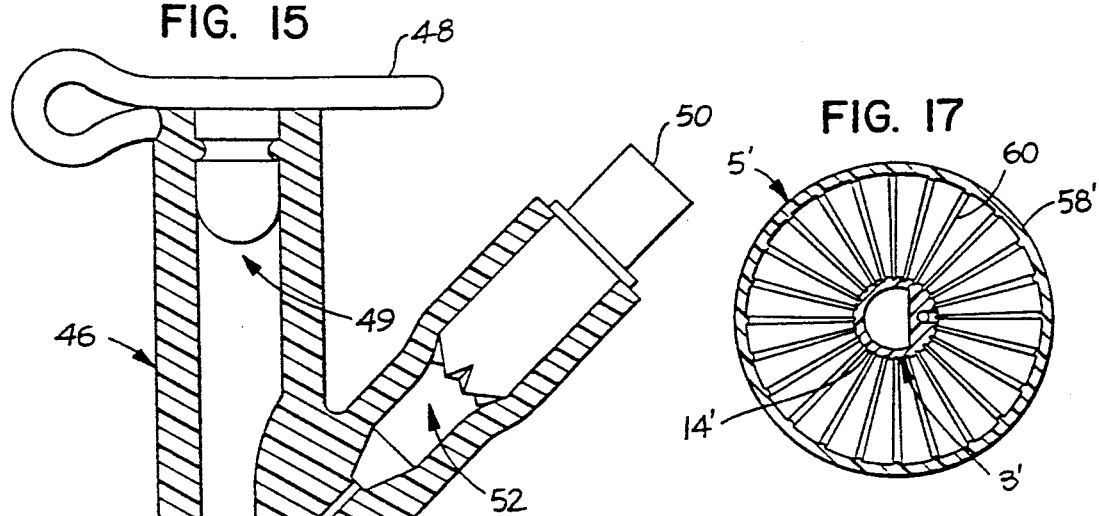
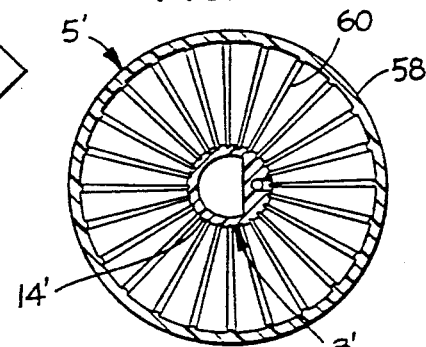
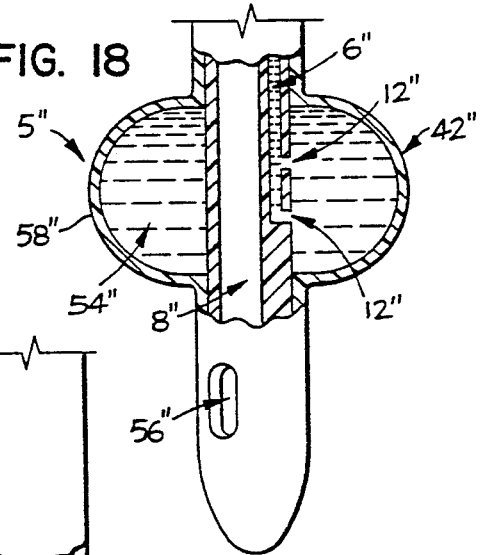
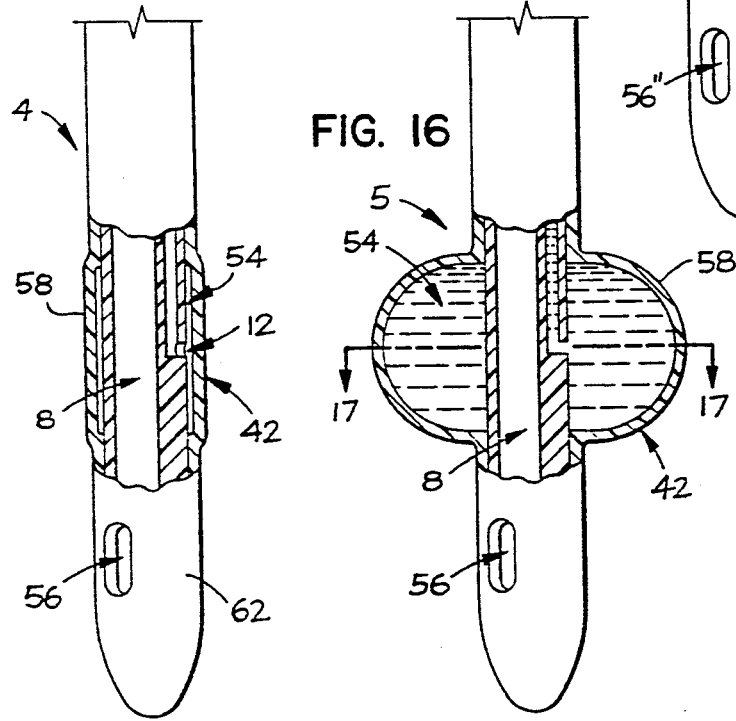

METHODS OF MAKING BALLOON CATHETERS

FIELD OF THE INVENTION

The present invention relates to balloon catheters and methods of making balloon catheters, such as "Foley" catheters and the like.

BACKGROUND OF THE INVENTION

Foley catheters are believed to be almost always made of either natural rubber (latex) or silicone rubber. Because of the different properties of these two compounds, standard manufacturing techniques currently believed to be used for each are somewhat different. Because the present invention is an improvement over these techniques, a description of each follows hereinbelow.

First, however, a short discussion of the products that are formed by these processes is presented as a foundation to clarify the advantages of the present invention. To this end, the Applicants note that silicone rubber catheters are considered to be superior to latex catheters because silicone rubber is believed to be more biocompatible. Studies suggest that silicone rubber catheters cause less adjacent cell death, are less likely to become encrusted, thereby minimizing resulting blockage and/or trauma upon withdrawal, and are more resistant to bacterial colonization. Silicone rubber is also more expensive than natural rubber, however, and, as will be explained below, the standard manufacturing process for silicone catheters has, heretofore, been more labor intensive and, therefore, more costly than the standard manufacturing process for latex catheters. As a result, silicone catheters are generally more expensive than latex catheters and, although believed to be medically superior, are not as widely used as the less expensive latex catheters.

The manufacturing processes of the present invention, which are disclosed and claimed hereinbelow, will allow silicone catheters produced using these processes to be price competitive with the latex catheters, and also provides for certain design advantages over currently available silicone catheters. In order to appreciate the simplicity of the present invention, however, the discussion of the standard manufacturing techniques used to produce the balloon portion of latex and silicone rubber Foley catheters is now presented below.

A. Latex Catheters

The double lumen tubing on which the balloon must be placed is normally made by dipping thin rods (mandrels) into a suspension of natural rubber (latex). The rubber is heat cured over the mandrels, and then the mandrels are withdrawn from the vulcanized rubber, leaving a length of double lumen tubing on which the balloon must be affixed. An opening is then punched in the tube which communicates with the smaller of the two lumens, called the capillary lumen. Then, a thin band of cured rubber, which has been manufactured and cured in a completely separate operation, is slipped over the tube by hand to form a sheath around the tube, and positioned so that it covers the opening that has been punched into the tube. In order to fix the distal and proximal ends of the band to the tube to form the balloon, the entire length of the tube is then dipped in latex, which creates an overcoat layer and bonds the band to the tube proximate the distal and proximal ends of the band, thereby forming the balloon. This step also adds to the thickness of the balloon and is used to adjust the outer diameter of the tube to the desired size. This process, therefore, involves both a hand operation requiring skilled labor, and a separate fabrication step necessary to manufacture the band that is used to provide the inner layer of the balloon.

B. Silicone Rubber Catheters

State of the art silicone rubber balloon catheter manufacture is considerably more expensive and time consuming than the corresponding process for latex catheters. The double lumen tubing is generally made by an extrusion process. This step is often automated and relatively inexpensive. The double lumen tubing must subsequently be cut to length and given both a rounded tip at the distal end and a balloon over an opening communicating with one of the two lumens. The approach used for latex balloon catheter manufacturing, slipping a band or a sleeve over the opening and then dipping the tube in a rubber solution, will not work for silicone rubber catheters. This is because silicone rubber dip solutions are solvent based, not water based. Any attempt to dip the sleeve in a silicone rubber solvent solution will cause the thin sleeve or band to enlarge and swell. The silicone rubber dip solution will then run in under the sleeve after passing through it, and will bond the entire inner surface of the sleeve to the tube.

Two approaches are believed to be in current use to add the rounded tip and the balloon to the double lumen tube to make silicone rubber Foley catheters. The first approach employs a method wherein the rounded tip and the balloon are formed as a single unit by process of injection molding. This single unit is then fixed to the extruded double lumen tube by hand. The process of attaching the balloon portion to the tube is time consuming, labor intensive and, consequently, quite expensive. The second approach method involves making a tip and a band or balloon portion separately. The band or balloon portion is formed by either dipping or injection molding. It is then slipped over the extruded tubing and positioned over a hole previously punched into the smaller of the two lumens in the same manner employed to manufacture latex catheters. Then, however, a worker "glues" both ends of the band to the extruded tubing by hand with a silicone rubber adhesive. The rounded tip is then attached by inserting the tube into a mold containing the preformed tip and essentially molding the tip onto the tube. This method is also time consuming, labor intensive and, therefore, relatively expensive.

Accordingly, it will be appreciated that there is a need for an efficient, price competitive method of making balloon catheters which will be an improvement over the aforementioned prior art methods. The present invention provides advantages over the prior art methods for manufacturing balloon catheters, and also offers other advantages over the prior art and solves other problems associated therewith.

SUMMARY OF THE INVENTION

Accordingly, it is an object of the present invention to provide a cost effective method of making balloon catheters. The present invention includes a method of making a balloon catheter comprising the steps of (a) providing a tube having an outer surface and plurality of lumens including first and second lumens, the tube including a first lumen access opening in the outer surface communicating with the first lumen; simultaneously coating a first portion of the outer surface with an amount of a bond preventing agent effective to prevent bonding to the first portion of the outer surface and plugging the first lumen access opening; and (c) subsequent coating a second portion of the outer surface and the coating of bond preventing agent on the first portion of the outer surface with a polymeric bonding composition, wherein a resilient overcoat layer is created which is fixed to and integral with the tube proximate the second portion of the outer surface and free from adherence to the tube proximate the first portion of the outer surface. Preferably, step (b) includes dipping the tube in a removable bond preventing agent such that the first portion of the outer surface is coated with a removable layer of the bond preventing agent and the first lumen access opening and a portion of the first lumen is filled with the removable bond preventing agent. Prior to step (c), step (b) is preferably followed by a step of stripping the removable bond preventing agent from a third portion of the outer surface, wherein the resilient overcoat layer created as a result of step (c) is fixed to and integral with the tube proximate the third portion of the outer surface, and wherein a balloon portion of the overcoat layer is located proximate the first portion of the outer surface.

In an alternate embodiment, a method of mass producing balloon catheters is provided. This method comprises (a) providing a plurality of tubes, each tube having the aforementioned elements; (b) simultaneously coating a portion of each tube and plugging the first lumen access opening of each tube; and (c) subsequently dipping each tube in a polymeric composition to form an overcoat layer wherein the overcoat layer includes a balloon portion proximate the coated portion of the tube. Further elements of these and further alternate embodiments of the present invention are disclosed hereinbelow.

It will be appreciated from a further review of the present invention that the methods of the present invention provide great advantages over the prior art methods of making balloon catheters which generally employ significant amounts of hand labor, sometimes for particularly delicate operations which are likely to have inconsistent results. On the other hand, because balloon catheters made using the methods of the present invention can be mass produced, and because the need for hand labor is minimized, the quality of the balloon catheters produced is consistent and the expense involved in the production of the catheters is price competitive with latex catheters manufactured using current prior art methods. The most preferred embodiments of the invention can be completely automated, thereby eliminating the need for skilled labor. It will be appreciated that this will be a great advantage in making silicone rubber catheters, which are generally more desirable than latex catheters, except for the higher cost which is generally associated with the prior art catheters made of silicone rubber. The applicants also note that the present methods allow the balloon portion of the silicone rubber catheters to have an outside diameter which is more consistent with the outside diameter of other portions of the balloon catheter than is generally observed with silicone rubber balloon catheters having balloon portions which have been affixed to the outer surface of a tube by hand.

These and various other advantages and features of novelty which characterize the present invention are pointed out with particularity in the claims annexed hereto and forming a part hereof. However, for a better understanding of the present invention, its advantages and other objects obtained by its use, reference should be made to the drawings, which form a further part hereof, and to the accompanying descriptive matter, in which there is illustrated and described preferred embodiments of the present invention.

BRIEF DESCRIPTION OF THE DRAWINGS

In the drawings, in which like reference numerals indicate corresponding parts throughout the several views.

FIG. 9 is a transverse schematic view of an intermediate tube similar to the tube shown in FIG. 7 at an intermediate stage of manufacture prior to the first of a series of dipping steps;

FIG. 10 is a transverse schematic view of an intermediate tube similar to that shown in FIG. 9, but following a first dipping step wherein the outer surface is coated with a bond preventing agent up to the point designated by line A;

FIG. 11 is a cross-sectional view of the intermediate tube of FIG. 10 as shown from the line 11—11;

FIG. 12 is a view of an intermediate tube similar to that shown in FIG. 10, but after a subsequent dipping step or steps in which the coating of bond preventing agent on a portion of the outer surface of the intermediate tube has been removed;

FIG. 13 is a transverse schematic view of a portion of a balloon catheter formed from the intermediate tube shown in FIG. 12, following a plurality of dipping steps to create an overcoat layer;

FIG. 14 is a cross-sectional view of the balloon catheter shown in FIG. 13 from the line 14—14;

FIG. 15 is a transverse schematic view of a Foley catheter made in accordance with the present invention following testing and cleaning and showing sectional views of portions thereof;

FIG. 16 is a schematic view of a portion of the Foley catheter shown in FIG. 15, but with the balloon portion of the catheter shown when expanded;

FIG. 17 is a cross-sectional view of an alternate embodiment of the Foley catheter shown in FIG. 16 as that embodiment would be seen from a line similar to the line 17—17 of FIG. 16, were FIG. 16 to show that embodiment;

FIG. 18 is a transverse schematic view similar to that shown in FIG. 16, but showing another alternate embodiment of a Foley catheter made in accordance with the present invention and including a plurality of first lumen access openings;

DETAILED DESCRIPTION OF THE PREFERRED EMBODIMENTS

Figure 1:
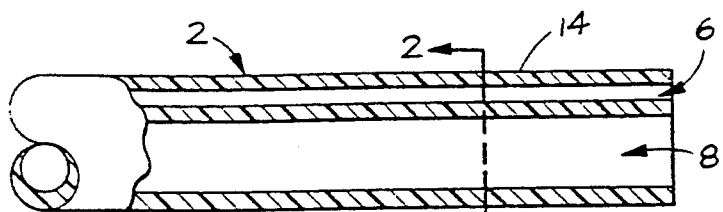
FIG. 1 is a transverse schematic view of an extruded double lumen tube in partial cross-section.
Figure 2:
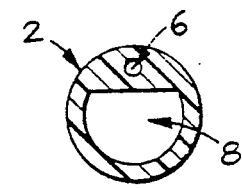
FIG. 2 is a cross-sectional view of the extruded double lumen tube as seen from the line 2—2 of FIG. 1.

Referring now to the drawings, and specifically to FIGS. 1 and 2, the first step in making a balloon catheter in accordance with the present invention is providing a double lumen tube 2, which is preferably extruded and made of silicone rubber. It will be appreciated, however, that the double lumen tube can be made by any known process which yields a double lumen tube. It will be further appreciated that the tube can be made of any resilient polymeric material, preferably a biocompatible polymeric material which can be inserted into a human body cavity. The double lumen tube 2 includes a smaller capillary lumen 6 and a larger fluid conduit lumen 8.

Figure 3:
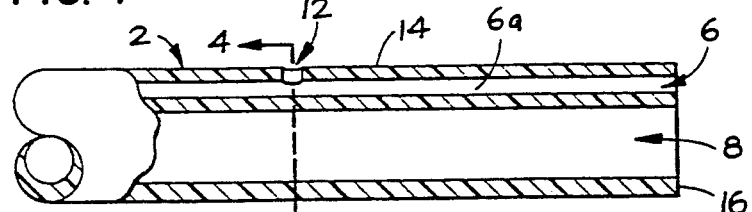
FIG. 3 is a transverse schematic view of the tube shown in FIG. 1 after an opening is punched in the outer surface.
Figure 4:
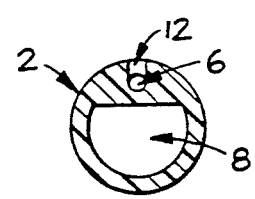
FIG. 4 is a cross-sectional view of the tube as shown from the line 4—4 of FIG. 3.

Referring now also to FIGS. 3 and 4, after the double lumen tube is cut to a desired size, a capillary lumen access opening 12 is created in an outer surface 14 of the double lumen tube 2. The capillary lumen access opening 12 communicates with the capillary lumen 6.

Figure 5:
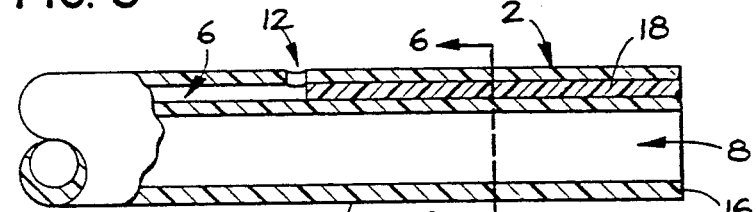
FIG. 5 is a transverse schematic view of the double lumen tube shown in FIG. 3 after a portion of the first lumen has been filled with a polymeric bonding composition.
Figure 6:
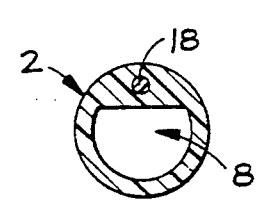
FIG. 6 is a cross-sectional view of the tube as seen from the line 6—6 of FIG. 5.
Figure 7:
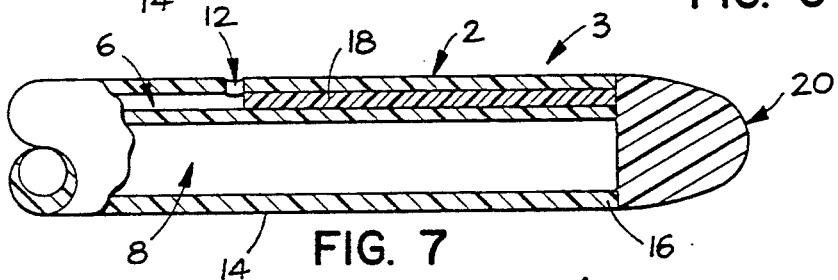
FIG. 7 is a transverse schematic view of the double lumen tube shown in FIG. 5 after a tip is affixed to a distal end of the tube.
Figure 8:
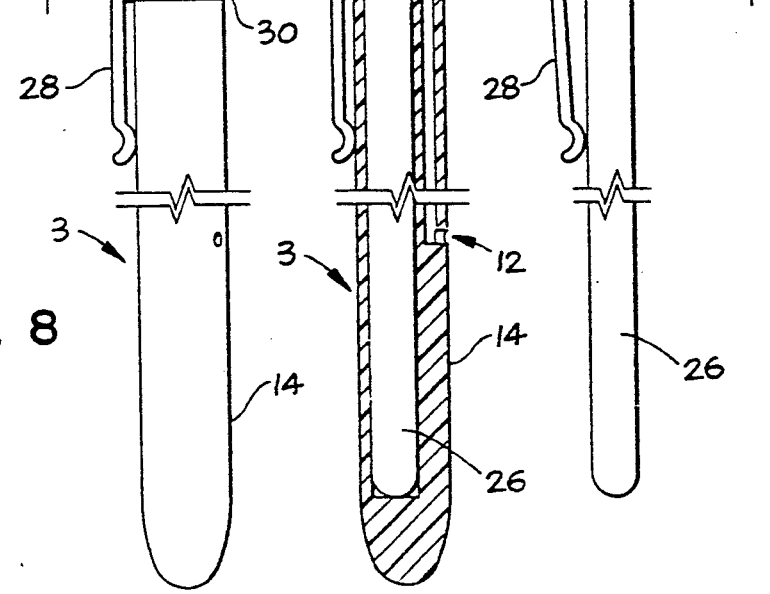
FIG. 8 is a schematic view of a portion of a rack used to retain a plurality of tubes during a series of steps designed to provide the tube with an overcoat layer of a polymeric bonding composition.
Figure 19:
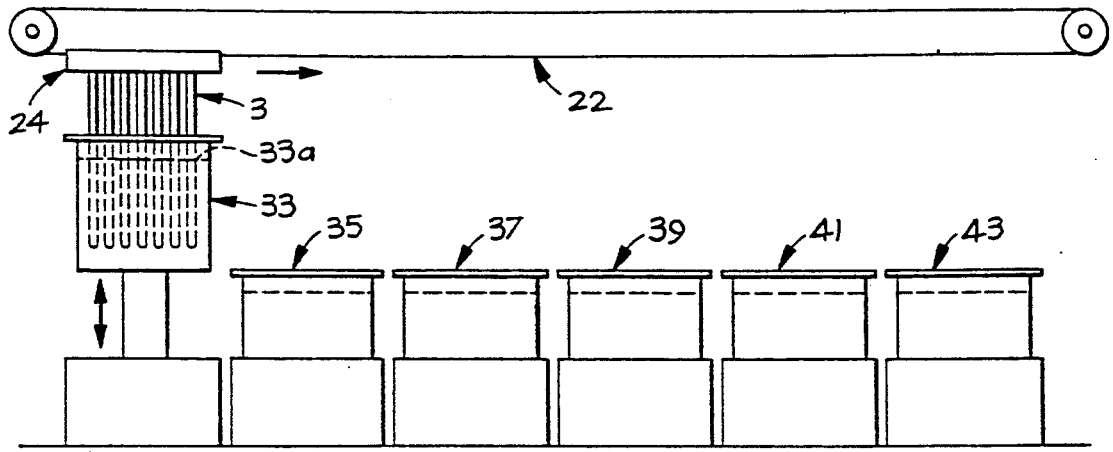
FIG. 19 is a schematic illustration of apparatus used to automate the production of balloon catheters in accordance with the present invention.

Referring now to FIGS. 5-7, an intermediate tube 3 is subsequently prepared from the double lumen tube 2 shown in FIG. 3. In the first step of this process, a measured amount of a polymeric bonding composition, preferably silicone rubber or another suitable polymeric bonding material, is injected into the capillary lumen 6 from the distal end 16 of the double lumen tube 2, so that the capillary lumen 6 is filled with a polymeric fill material 18 up to a point just below the capillary lumen access opening 12. A tip 20, preferably a rounded silicone rubber tip, is then affixed to the distal end 16 of the tube 2 to complete the formation of the intermediate tube 3 shown in FIG. 7. In a preferred method, the distal end 16 of the tube 2 inserted into a molding apparatus (not shown) designed to mold a tip 20 on the end of the tube 2.

Referring now also to FIGS. 7-14 and 19, a preferred process of the present invention involves securing a plurality of intermediate tubes 3, like the intermediate 3 shown in FIG. 7, to a rack or pallet 24. The rack or pallet 24 will include a plurality of support rods 26, each equipped with a retaining clip 28. The intermediate tubes 3 are secured on the support rods 26 by engaging individual support rods 26 in the larger of the two lumens, called the fluid conduit lumen 8, and sliding the intermediate tubes 3 up over the support rods 26 until the proximal ends 30 of the intermediate tubes 3 abut against the base of the retaining clips 28 or, preferably, the tip 20 of each of the intermediate tubes 3 fits snugly against the distal tip of each of the support rods 26, as shown in FIGS. 9 and 10. Although not shown, it is believed that the intermediate tubes 3 can be secured on the support rods 26 without the aid of the retaining clips 28. This is because the preferred extruded double lumen tubes 2 used to make the intermediate tubes 3 generally have a slight bend in one direction or another when they are hung. This results in a slight bend in the intermediate tubes 3 that permits the intermediate tube 3 to be secured on a support rod 26 without the aid of a clip 28. Because of the nature of the polymeric materials generally used to make the intermediate tubes 3, they also have a tendency to cling to other surfaces and to offer resistance to movement of a surface along a surface of this material.

When the intermediate tubes 3 have been secured on the support rods 26, the pallet 24 can be transferred from place to place, and the intermediate tubes 3 on the pallet 24 can be dipped in a series of baths (see FIG. 19) prepared to accomplish a series of process steps. In the preferred method of the present invention, the intermediate tube 3 is made entirely of silicone rubber and is secured upon a support rod 26 made of spring steel. The tip 20 and the fill material 18 of the intermediate tube 3 shown in FIG. 7 are made of the same material (silicone rubber) as the double lumen tube 2. Therefore, the tip 20 and the fill material 18 form integral portions of the intermediate tube 3, which is shown in FIGS. 9-14 as an integral polymeric unit made of a single material.

The first step in the automated coating or dipping process of forming the balloon portion 32 of the balloon catheter 4 (shown in FIG. 13), after the intermediate tubes 3 are secured to the pallet 24, is to coat the intermediate tubes 3 with a bond preventing agent, preferably a removable bond preventing agent. Preferably this is accomplished by dipping each of the tubes 3 on the pallet 24 simultaneously into a first dip tank 33 containing a bath 33a of a removable bond, preferably a material which forms a semi-solid film on surfaces when cooled on contact followed by an opportunity for drying. Examples of such materials include petroleum jelly or petrolatum, other oil base substances which form a semisolid upon cooling to room temperature, liquid soaps which dry to form a semi-solid, aqueous soap or detergent solutions, aqueous or oil based film forming solids emulsions, and the like. In one embodiment described herein, hot petrolatum is used, and in another, a liquid soap is used, preferably Liquid Ivory Soap from Proctor & Gamble, Cincinnati, Ohio.

When the intermediate tubes 3 are removed from this first bath 33a of removable bond preventing agent, the agent adheres to the outer surface 14 of the intermediate tube 3, and enters the capillary lumen access opening 12 and runs up into the capillary lumen 6. In one embodiment the agent is petrolatum, which is heated to about 140°-160° F., preferably about 150° F. At these temperatures, the petrolatum will run up into the capillary lumen 6 through the capillary lumen access opening 12 with the assistance of the "capillary effect", which draws the fluid into the capillary lumen 6 to the level of the petrolatum in the first tank 33. As the intermediate tubes 3 are withdrawn from the hot petrolatum, petrolatum on each tube cools and solidifies to form a semi-solid coating 38 on the outer surface 14 and a semi-solid filling 34 in the capillary lumen 6 and the capillary lumen access opening 12 which cooperate to plug the capillary lumen access opening 12. IN an alternate embodiment, the bond preventing agent in the first tank 33 is liquid soap at room temperature (about 62°-74°). When the tubes 3 are withdrawn from the first dip tank 33, the liquid soap forms of semi-solid just as the hot petrolatum did as it cooled. Although both of these bond preventing agents are effective, there is some advantage to using the soap because it does not require the added expense for heating. Furthermore, it is believed soap is easier to remove from the capillary lumen 6 and the balloon cavity 54.

After the intermediate tubes 3 are coated and the capillary lumen access openings 12 are plugged simultaneously with bond preventing agent in this manner (see FIG. 10), the tubes 3 are then dipped in a series of dip tanks (see FIG. 19) provided to remove the bond preventing agent from a portion 14a of the outer surface 14 below the dashed line designated B. After this portion 14a of the outer surface 14 is substantially stripped of any residue of the bond preventing agent, the intermediate tubes 3, now partially coated with bond preventing agent between the dashed lines designated A and B as shown in FIG. 12, are dipped in a polymeric bonding composition, preferably silicone rubber, in a step or steps provided to coat the intermediate tube 3 to create the balloon catheter 4 shown in FIGS. 13-14. In the preferred methods, the intermediate tube 3 is dipped in silicone rubber in two or more successive dipping steps so that the resulting overcoat layer includes at least an underlying and an overlying layer, 43 and 44 respectively, which form an integral part of the balloon catheter 4 and are bonded together and to the outer surface 14 in the portions thereof, 14a and 14b, which are located below the dashed line designated B and above the dashed line designated A, respectively. The portion 14b above line A was not coated prior to the final dipping steps designed to provide the overcoat layer 42, and the portion 14a below line B was stripped of its coating prior to those steps.

In subsequent steps, the proximal end 30 of the balloon catheter 4 is secured to an end piece 46 to form a completed Foley catheter 5 (shown in FIG. 15). The end piece 46 can include a cap 48 for closing a proximal end access opening 49 to the fluid conduit lumen 8 and can be equipped with a luer valve 50 for engagement in and closure of the proximal capillary lumen access upper opening 52 communicating with the capillary lumen 6. Prior to the attachment of the end piece 46 to the balloon catheter 4 to form the completed Foley catheter 5, the completed balloon catheter 4 is preferably allowed to air dry to permit solvents in the overcoat layer 42 to evaporate and is subsequently cured at an elevated temperature. Care is taken to keep the curing temperature below the boiling temperatures of the solvent so as to prevent unsightly bubbling of the solvent within the overcoat layer 42. Because the overcoat layer 42 is made of the same polymeric bonding composition, even though it may be created in a plurality of dipping steps, it is represented in FIGS. 15-18 as a single overcoat layer 42. It will be appreciated, however, that this single overcoat layer 42 may or may not represent an integral layer formed in a series of dipping steps wherein there may be any number of underlying or overlying layers. The completed Foley catheter 5 also includes a fluid conduit access opening 56 in an exterior surface 62 of the completed Foley catheter 5. The fluid conduit access opening 56 communicates with the fluid conduit lumen 8.

In preferred methods in accordance with the present invention, the end piece 46 is made by a process of injection molding. Preferably, the proximal end 30 of the balloon catheter 4 is inserted into the injection molding apparatus after the overcoat layer 42 has been cured. The polymeric bonding composition, preferably silicone rubber, is then injected into the mold (not shown) and the end piece 46 is molded onto the proximal end 30 of the balloon catheter 4 to make the completed Foley catheter 5 shown in FIG. 15. Following further drying curing steps where deemed necessary given the type of polymeric bonding composition or compositions used to make the completed Foley catheter 5, the completed catheter 5 is tested to see if it is functional and if it has any leaks. This testing can be done before or after the fluid conduit access opening 56 is created in the exterior surface 62 to communicate with the fluid conduit lumen 8.

In order to test the integrity of the completed catheter 5, prior to engaging the plug 50 in the proximal capillary lumen access opening 52 in the end piece 46, the proximal capillary lumen access opening 52 is slipped over a hot water nozzle (not shown), and a measured amount of a hot aqueous solution, preferably water or water containing a trace of surfactant, at a temperature of between about 120°-160° F., preferably about 140° F., is pumped into the capillary lumen 6 from a standard hot water heater (not shown) by a commercially available water pump (not shown) such that the balloon portion 58 is expanded. The balloon portion 58 of the overcoat layer 42 is the portion of the overcoat layer 42 which is not bonded to the outer surface 14 of the intermediate tube 3. The balloon portion 58 of the overcoat layer 42 cooperates with the portion 14c of the outer surface 14 which remained coated with the bond preventing agent prior to the step of dipping the intermediate tube 3 in the polymeric bonding composition, to define a balloon cavity 54. The balloon cavity 54 communicates with the capillary lumen 6 via the capillary lumen access opening 12. When the hot water solution is pumped or injected into the capillary access lumen 6 to test the completed catheter 5 and the balloon portion 58, the balloon portion 58 and the balloon cavity 54 are expanded. If there is a significant lack of integrity in the balloon portion 58 it will be exposed when the water is introduced in this manner. In addition to testing the balloon portion 58, the water solution will also remove the remaining bond preventing agent in the balloon lumen 54 and the capillary lumen 6 when it is removed. Although some of the bond preventing agent may come out of the capillary lumen 6 via the proximal capillary lumen access opening 52 during the step of curing the overcoat layer 42, the hot aqueous solution is generally believed to remove most of the bond preventing agent, although a residue may remain.

Following the preliminary test, which relies on a visual observation to determine whether there is any lack of integrity, a further test is used to obtain further assurance that there are no leaks in the balloon portion 58. This further test is accomplished by engaging the proximal capillary lumen accessing opening 52 to the nozzle of a commercially available leak tester (not shown). One such device is a Model No. 6510 Caps Tester from Caps Himmelstein (Hoffman Estates, IL 60195). Once the completed catheter 5 is tightly secured over the nozzle, an electrical switch, such as a hand switch or, preferably, a foot pedal, is used to release a measured blast of air into the capillary lumen 6. When the air is introduced into the capillary lumen 6 it also enters the balloon cavity 54 via the capillary lumen access opening 12 and inflates the balloon portion 58 and, thereby, expands the balloon cavity 54. The leak tester is designed to sense any loss of pressure once the balloon portion 58 is inflated, and will given an indication, therefore, if there are any measurable leaks. After this test is completed, the completed catheters 5 that have passed all tests, are then packaged, preferably in a material which breathes such as Tyvek ™ (from DuPont), and boxed. The boxes are then sterilized with ETO (Ethylene Oxide) and then stored for shipment.

In a preferred embodiment of the present invention, the extruded double lumen tube 2 used to make the intermediate tube 3 is a tube 3' which has a series of generally parallel ribs running generally parallel with the longitudinal axis of the tube 3' (see FIG. 17). When such a tube 3' is used, a Foley catheter 5' having a ribbed inner surface 60 on the balloon portion 58' of the completed Foley catheter 5' will result because the bond preventing coating 38' (not shown) on the intermediate tube 3' will reciprocate the undulations in the ribbed outer surface 14' of the intermediate tube 3'. Therefore, when the balloon portion 58' of the overcoat layer is created, the inner surface 60 will reciprocate the undulations in the bond preventing coating material 38 coating the coated portion 14c' of the outer surface 14'.

Referring now also to FIG. 18, another embodiment of the present invention provides a completed Foley catheter 5" which has a plurality of capillary openings 12" that permit greater access to the balloon lumen 54" from the capillary lumen 6" and vice versa. This can be very important when wishing to ensure that the access to the capillary lumen 6" from the balloon lumen 54" is not blocked once the balloon portion 58" of the overcoat layer 42" is expanded.

In the Applicants' use of the preferred methods of the present invention, balloon fabrication is almost completely automated. Entire sets of balloon catheters 4 are manufactured simultaneously. The preferred pallet 24 has 400 spring steel support rods 26 attached to a pallet in 20 rows of 20 rods, wherein each of the rods 26 is about 1 inch from each adjacent rod. Double lumen tubing (not shown) is preferably made by an extrusion process which is known to those of skill in the art. The tubes 2 are cut to length as the tubing leaves the extruder (not shown). An opening 12 is created in the outer surface 14, preferably with a hollow drill bit or tube (not shown), so as to communicate with the capillary lumen 6. The distal portion 6a of the capillary lumen 6, located between the distal end 16 of the tube 2 and the capillary lumen access opening 12, is injected with a measured amount of a polymeric bonding composition, preferably silicone rubber, so that the distal portion 6a is filled and sealed. A rounded tip 20 is preferably formed at the distal end 16 of the double lumen tube 2 by inserting the tube 2 in a molding device (not shown).

In the most preferred embodiments of the present method, 400 of the intermediate tubes 3 are then mounted vertically on rigid spring steel support rods 26 on a pallet 24 in the manner previously described. The pallet 24 is then moved via a transporting mechanism 22 (see FIG. 19) over a series of dip tanks as follows in one of these embodiments:

(A) The pallet 24 is stopped over a first tank 33, which contains white USP petrolatum heated to about 67° C. (about 150° F.). The tank is raised so as to immerse the intermediate tubes 3 into the petrolatum to such a depth that the petrolatum reaches the proximal end of the desired balloon location. The dip tank 33 is then lowered and a portion of the outer surface 14 of the intermediate tubes 3 are coated with petrolatum. This portion extends from the point at which the proximal end of the balloon portion 58 will begin to the distal end of the tip 20 of the intermediate tube 3.

(B) The pallet 24 is then automatically advanced and stopped over a second dip tank 35 which contains white USP petrolatum heated to about 120° C. (about 250° F.). The second dip tank 35 is raised so as to immerse the intermediate tubes 3 into the super-heated petrolatum so that the super-heated petrolatum comes into contact with the petrolatum coating on outer surface 14 of the intermediate tube 3 from the prior dipping step up to a location where a distal end of the balloon portion 58 will end. The second dip tank 35 is then lowered. This dipping step causes the coating of petrolatum from the prior dipping step to be largely removed from a portion 14a of the outer surface 14 of the intermediate tube 3 from a location where the distal end of the balloon lumen 54 will be located (designated by dashed line B) to the distal end 20a of the tip 20 of the intermediate tube 3. Some residual petrolatum may remain on the outer surface 14 of the intermediate tube 3 in this portion 14a of the outer surface 14. However, most of the petrolatum is removed.

(C) The pallet 24 is then automatically advanced and stopped over a third dip tank 37 containing mineral spirits heated to about 200° F. The third dip tank 37 is then raised so as to immerse the intermediate tubes 3 into the mineral spirits to the same depth as they were immersed in the super-heated petrolatum in the second dip tank 35. The tank 37 is then lowered and all but a trace amount of the petrolatum is removed from the portion 14a of the outer surface 14 below the portion 14c of the outer surface 14, which will eventually be proximate the balloon lumen 54.

(D) The pallet 24 is then automatically advanced and stopped over a fourth dip tank 39 containing a volatile organic solvent such as toluene, trichloroethane or the like. The fourth tank 39 is then raised to immerse the intermediate catheters 3 to the same depth as previously immersed in the second and third tanks 35 and 37, thereby removing essentially all traces of the petrolatum from this portion 14a of the outer surface 14. The intermediate catheter tube 3 now has a band 38 of semi-solid petrolatum located around the axial circumference of the intermediate tube 3 in the location where the balloon cavity 54 will be created. The petrolatum not only coats the portion 14c of the outer surface 14 located in this area, but also fills a portion of the capillary lumen 6 and plugs the capillary lumen access opening 12, which will eventually be used to inflate the balloon portion 58 of the completed Foley catheter 5.

(E) The pallet 24 is then lowered and automatically advanced to a fifth dip tank 41 containing a low-solids hexamethyl disiloxane or toluene silicone rubber solution which is effective to minimize any disruption of the integrity of the petrolatum coating 38 remaining on the intermediate tube 3 proximate the portion 14c of the outer surface 14 where the balloon lumen 54 will be created during subsequent dipping steps. The fifth tank 41 is then raised to immerse essentially the entire length of the intermediate tube 3 in the solution. This step can be subsequently repeated at intervals, preferably allowing time for significant solvent evaporation, either in the same tank or in a subsequent tank containing a greater concentration of silicone rubber, until the overcoat layer 42 and the balloon portion 58 of the overcoat layer 42 have a desired balloon thickness. Alternatively, the tank 41 is lower, the palled 24 is advance to a sixth dip tank 43 contain a silicone rubber solution having a higher silicone rubber concentration and the tubes 3 are completely immersed again. The preferred thickness over the overcoat layer 42 and the balloon portion 58 is 17.5 thousandths of an inch (plus or minus 2.5 thousandths of an inch). Where subsequent silicone rubber dip tanks are provided, the concentration of silicone rubber in the subsequent tanks are preferably greater than the concentration of the silicone rubber in the fifth tank 41. It is desirable to alter the silicone rubber used in the final coating to provide greater sheen and a smoother finish, however, the concentration and the solvent may be adjusted as deemed appropriate.

(F) The pallet is then advanced through a drying area where solvents are allowed to evaporate, and then through a heat cure step, where the balloon catheters 4 formed by this process are cured at a temperature just below the boiling point of any solvent used in any of the silicone rubber dip solutions. For toluene this temperature is about 200° F.

(G) After the heat cure, the balloon catheters 4 are allowed to cool and are then removed from the support rods 26. The proximal ends 30 of each of the balloon catheters 4 is then inserted into an injection molding apparatus (not shown), which forms the end piece 46 of the completed Foley catheter 5.

(H) The completed Foley catheters 5 are then finished by punching a fluid conduit access opening 56 in the exterior surface 62 such that it communicates with the fluid conduit lumen 8 in a location below or distal to the balloon portion 58 of the overcoat layer 42.

(I) The completed Foley catheters 5 are then sent through the test sequence described hereinabove, during which the balloon portion 58 of each completed Foley catheter 5 is inflated and the petrolatum band 38 within the balloon cavity 54 is largely removed.

Figure 20A:
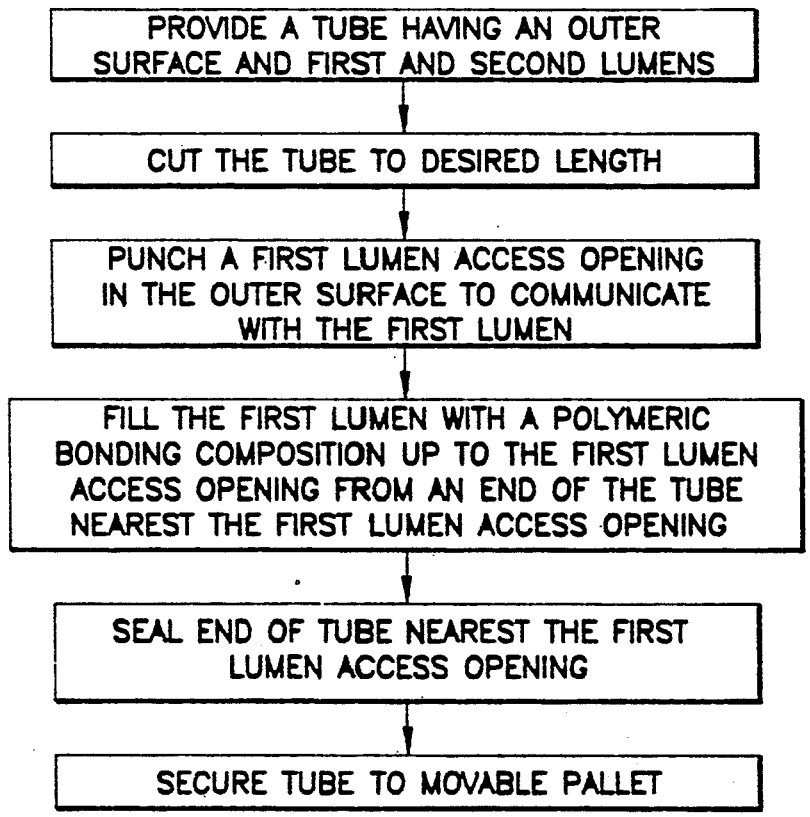
FIG. 20a, 20b and 20c are flow charts representing certain steps in accordance with the present invention.
Figure 20B:
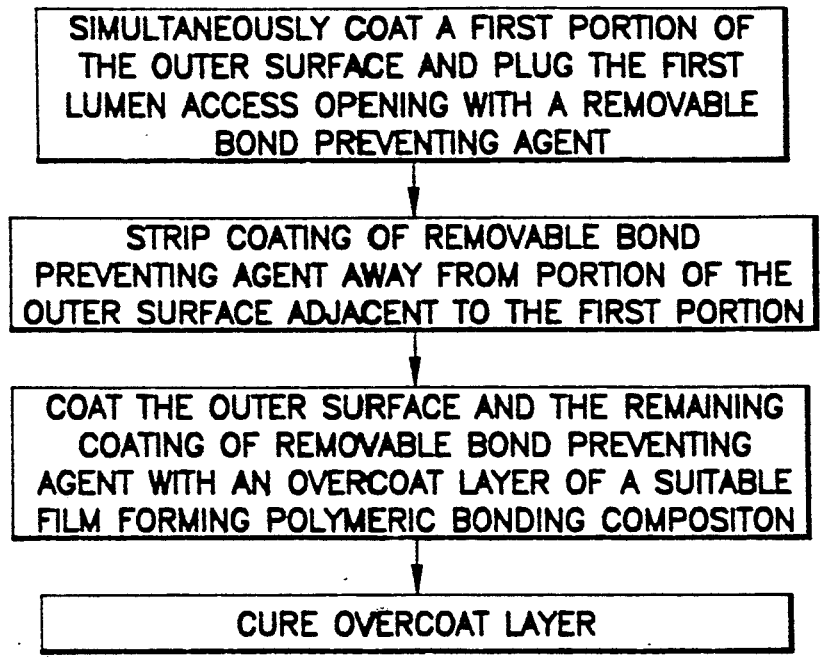
Figure 20C:
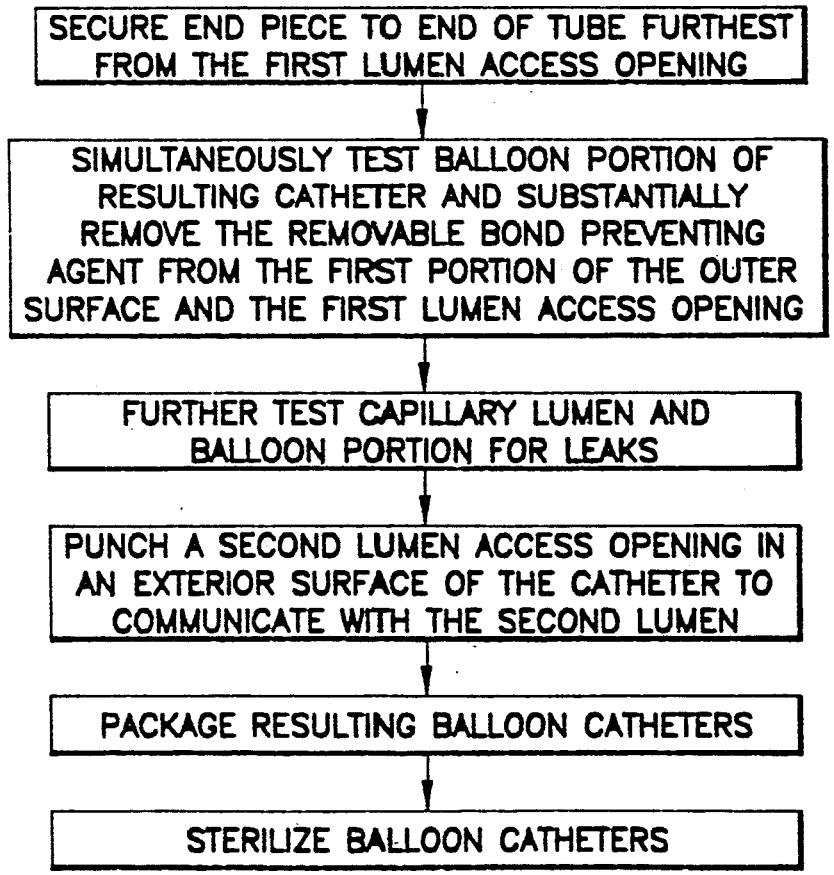

Referring now to FIGS. 20a, 20b and 20c, the present invention provides a method of making balloon catheters including the following steps:

(A) Providing a tube having an outer surface and first and second lumens;
(B) Cutting the tube to a desired length;
(C) Creating a first lumen access opening in the outer surface to communicate with the first lumen;
(D) Filling the first lumen with a polymeric bonding composition up to the first lumen access opening from an end nearest the first lumen access opening;
(E) Sealing the end of the tube nearest the first lumen access opening; and
(F) Securing the tube to a movable pallet.

These steps are followed by the following steps:
(A) Simultaneously coating a first portion of the outer surface and plugging the first lumen access opening with a removable bond preventing agent;
(B) Stripping the coating of removable bond preventing agent away from a portion of the outer surface adjacent to the first portion;
(C) Coating the outer surface and the remaining coating of removable bond preventing agent with an overcoat layer of a suitable film forming polymeric bonding composition; and
(D) Curing the overcoat layer.

Following those steps, methods of the present invention include the following steps:
(A) Securing an end piece to the end of the tube furthest from the first lumen access opening;
(B) Simultaneously testing the balloon portion of the resulting catheter and substantially removing the removable preventing bond agent from the first portion of the outer surface and the first lumen access opening;
(C) Further testing the catheter capillary lumen and the balloon portion for leaks;
(D) Punching a second lumen access opening in an exterior surface of the catheter to communicate with the second lumen;
(E) Packaging the resulting balloon catheters; and
(F) Sterilizing the balloon catheters.

In another preferred embodiment of the present invention following the securing of a plurality of intermediate tubes 3 to the transportable pallet 24, balloon catheters are produced as follows:

(A) The pallet 24 is stopped over a first tank 33, which contains a liquid soap (Liquid Ivory Soap from Proctor & Gamble Co., Cincinnati, OH 45202). The soap is held at room temperature (between about 60°-80° F., preferably 65°-72° F.). The dip tank 33 is raised so as to immerse the intermediate tubes 3 into the liquid soap so that the soap coats the tubes 3 up to the dashed line designated by the letter A in FIG. 10. The dip tank 33 is then lowered and the liquid soap forms a semi-solid coating 38 on the outer surface 14 of each of the intermediate tubes extending from line A to the distal end of the tip 20 of the intermediate tubes 3.

(B) The pallet 24 is then automatically advanced and stopped over a second dip tank 35 which contains an aqueous solution containing a trace of a suitable wetting agent or surfactant. In a preferred embodiment, three gallons of water is mixed with two ounces of a suitable surfactant. The surfactant will generally be less than one percent of the total volume of the solution. A second dip tank 35 is then raised so as to immerse the intermediate tubes 3 in the aqueous fluid up to the dashed line designated by the letter B in FIGS. 10 and 12. The second dip tank 35 is then lowered and the semi-solid liquid soap coating the portion 14a of the outer surface 14 below the dashed line designated B is substantially removed.

(C) The pallet 24 is then automatically advanced and stopped over a third dip tank 37 containing water. The third dip tank 37 is then raised and the intermediate tubes are immersed in the water up to the line designated B as in the prior dipping step. The third dip tank 37 is then lowered and virtually all of the liquid soap is removed from the portion 14a of the outer surface 14 below the line designated B.

(D) The pallet 24 is then automatically advanced and stopped over a fourth dip tank 39 containing a low-solids hexamethyl disiloxane or toluene silicone rubber solution which is effective to minimize any disruption of the integrity of the liquid soap coating 38 remaining on each of the intermediate tubes proximate the portion 14c of the outer surface 14 where the balloon lumen will be created during subsequent dipping steps (the portion between the dashed lines designated A and B). The fourth tank 39 is then raised to immerse essentially the entire length of each of the intermediate tubes 3 in the silicone rubber solution. It will be appreciated that other organic solvents such as toluene, and the like may be substituted for the hexamethyl disiloxane solvent used in this example. It will also be appreciated that this step can be repeated at subsequent intervals, preferably long enough to permit significant solvent evaporation, to add to the thickness of the overcoat layer 42 and the balloon portion 58 of the overcoat layer 42. However, further steps, involving different solutions can also follow.

(E) The fourth dip tank 39 is then lowered and the silicone rubber, coating portions of the outer surface 14 as well as the coating of soap 38, is allowed to dry. The pallet 24 is then advanced again to a fifth dip tank 41 preferably containing a different silicone rubber solution having a solids content which is higher than the solids content in the fourth dip tank 39. The intermediate tubes are immersed again in the subsequent silicone rubber solution when the fifth dip tank 41 is raised. The fifth dip tank 41 is then lowered, and the silicone rubber coating the tubes 3 is allowed to dry.

(F) The pallet 24 is then automatically advanced again to a sixth dip tank 43 containing a silicone rubber solution including a silicone rubber which provides a high sheen and a smooth texture surface. The tubes are dipped again as before and the sixth dip tank 43 is then lowered and the silicone rubber coating the tubes 3 is allowed to dry.

(G) The pallet 24 is then advanced through a drying step followed by a heat cure step, and each completed balloon catheter 4 is then secured to an end piece, tested, provided with a fluid conduit access opening 56, packaged and sterilized.

The automated system that Applicants claim will permit completed Foley catheters 5 to be manufactured at the rate of about 1,600 catheters per hour. Because no handwork is involved, the catheters 5 produced will be consistent and of very high quality. The exterior surface 62 is smoother than hand-glued balloons, and the outside diameter of the balloon portion 58 is essentially identical to the outside diameter of other portions of the completed Foley catheters 5. It will be appreciated that larger outside diameter balloon portions are undesirable since they are somewhat more difficult to insert and withdraw, and cause additional trauma upon withdrawal. In addition, by eliminating the hand labor involved in adhering the balloon portion 58 to the intermediate tube 3 in the manufacture of silicone rubber balloon catheters 4, by specifically eliminating the separate step of fabricating the balloon portion, which also requires hand labor, and by eliminating the significant impact on yield resulting from hand processing errors, the applicants' new process will permit direct production cost for silicone rubber balloon catheters of all types to be reduced by about 25-50% over the cost estimated for the prior art silicone rubber balloon catheters.

It is to be understood, however, that even though numerous characteristics and advantages of the present invention have been set forth in the foregoing description, together with details of the structure and function of the invention, the sequence or order of the specific steps, or the actual compositions, solvents, temperatures, environmental conditions and the like employed for each step, it will be appreciated the disclosure is illustrative only, and that changes may be made in detail, especially in matters of shape, size, arrangement of parts or sequence or elements of events within the principles of the invention to the full extent indicated by the broad general meaning of the terms in which the appended claims are expressed.

What is claimed is:

1. A method of making a balloon catheter, said method comprising the steps of:
    (a) providing a tube having an outer surface and a plurality of lumens including first and second lumens, said tube including a first lumen access opening in said outer surface communicating with said first lumen;
    (b) dipping the tube in a removable liquid bond preventing agent, and thereby simultaneously forming a coating on first and third adjacent portions of the outer surface with an amount of the bond preventing agent effective to prevent bonding to the first portion of the outer surface, and filling the first lumen access opening and at least a portion of the first lumen;
    (c) stripping the coating of removable bond preventing agent from the third portion of the outer surface; and
    (d) subsequently coating a second portion and the third portion of the outer surface and the coating of bond preventing agent on the first portion of the outer surface with a polymeric bonding composition; and wherein a resilient overcoat layer is created which is fixed to and integral with the tube proximate the second and third portions of the outer surface and free from adherence to the tube proximate the first portion of the outer surface, and wherein a balloon portion of the overcoat layer is located proximate the first portion of the outer surface.

2. The method of claim 1 wherein step (a) includes extruding the tube, cutting the tube to a desired length, creating the first lumen access opening in the first portion of the outer surface, introducing a measured amount of a polymeric bonding composition into the first lumen such that a section of the first lumen is filled with said polymeric composition, and adding a tip to a distal end of the tube such that access to the respective lumens via the distal end is restricted.

3. The method of claim 1 wherein the tube has a tip and distal and proximal ends, access to said first and second lumens from said distal end being restricted by the tip, wherein said step of stripping the coating of removable bond preventing agent from the third portion of the outer surface includes dipping the third portion of the outer surface in a fluid or fluids to remove the coating of removable bond preventing agent therefrom.

4. The method of claim 1 wherein step (d) is followed by a step of securing an end piece to a proximal end of the tube, the end piece including proximal openings communicating with the first and second lumens respectively.

5. The method of claim 1 wherein step (d) is followed by a step of creating a second lumen access opening in an exterior surface which communicates with the second lumen.

6. The method of claim 1 wherein step (d) is followed by introducing an amount of hot aqueous fluid into the first lumen and a balloon cavity defined by the balloon portion of the overcoat layer and the first portion of the outer surface, said balloon lumen being in communication with said first lumen via said first lumen access opening, wherein the step of introducing hot aqueous fluid is followed by the step of removing the aqueous fluid, said aqueous fluid acting as a carrier to substantially remove the removable bond preventing agent from the first lumen, the first lumen access opening and the balloon cavity.

7. A method of making a balloon catheter from a tube having an outer surface and a plurality of lumens, the tube having first and second lumens, distal and proximal ends and a first lumen access opening in the outer surface which communicates with the first lumen, said method including the steps of:
 (a) dipping the tube in a removable liquid bond preventing agent effective to coat first and third adjacent portions of the outer surface and to fill the first lumen access opening and at least a portion of the first lumen;
 (b) dipping the tube in a fluid or fluids in one or more dipping steps such that the removable bond preventing agent is substantially stripped from the third portion of the outer surface of the tube; and
 (c) subsequently coating the tube with a polymeric composition which bonds to a second portion and the third portion of the outer surface and forms an overcoat layer which is integral with the tube proximate the second and third portions of the outer surface, and wherein the second and third portions of the outer surface are opposite one another and adjacent to the first portion of the outer surface, wherein the overcoat layer proximate the first portion of the outer surface is free from adherence thereto and forms a balloon portion of the overcoat layer and the balloon portion cooperates with the first portion of the outer surface to define a balloon cavity which communicates with the first lumen via the first lumen access opening.

8. A method of claim 7 wherein step (a) is preceded by a step of introducing a polymeric bonding composition into the first lumen, wherein the bonding composition bonds to the tube within the first lumen between the distal end of the tube and the first lumen access opening, and a step of forming a tip at the distal end of the tube which restricts communication with the first and second lumens proximate the distal end of the tube.

9. A method of making a balloon catheter from a tube having an outer surface and a plurality of lumens, the tube having first and second lumens and distal and proximal ends, the outer surface including a first lumen access opening which communicates with the first lumen, the first lumen extending from the first opening to the proximal end of the tube, the distal end of the tube including a tip which prevents communication with the first and second lumens proximate the distal end of the tube, said method including the steps of:
 (a) dipping the tube in a removable liquid bond preventing agent effective to form a coating on the outer surface of the tube such that areas of the outer surface which are coated with the removable bond preventing agent are generally inaccessible for the purpose of bonding therewith, wherein the removable bond preventing agent fills the first lumen access opening and at least a portion of the first lumen and coats first and third adjacent portions of the outer surface, said first lumen access opening being located in the first portion of the outer surface;
 (b) dipping the tube in a fluid or fluids in one or more dipping steps such that the removable bond preventing agent is substantially stripped from the third portion of the outer surface adjacent to the first portion and opposite to a second portion with respect to the first portion; and
 (c) subsequently dipping the tube in a polymeric bonding composition to form a resilient overcoat layer which bonds to the second and third portions of the outer surface and coats the removable coating of bond preventing agent on the first portion of the outer surface; wherein the resilient overcoat layer is fixed to and integral with the tube proximate the second and third portions of the outer surface and is free from adherence to the tube proximate the first portion of the outer surface, wherein the overcoat layer includes a balloon portion, said balloon portion being the portion of the overcoat layer proximate to the first portion which is free from adherence to the outer surface, wherein the balloon portion of the overcoat layer and the first portion of the outer surface cooperate to define a balloon cavity which communicates with the first lumen via the first lumen access opening.

10. A method of mass producing balloon catheters, said method comprising:
 (a) providing a plurality of tubes, each tube having an outer surface and a plurality of lumens including first and second lumens, each of said tubes including a first lumen access opening in said outer surface communicating with said first lumen;
 (b) simultaneously dipping each tube in a removable liquid bond preventing agent and thereby simultaneously forming a coating on first and third adjacent portions of the outer surface and filling the first lumen access opening and at least a portion of the first lumen of each tube with the bond preventing agent;
 (c) stripping the coating of removable bond preventing agent from the third portion of the outer surface of each tube; and
 (d) subsequently dipping each tube in a polymeric bonding composition such that a resilient overcoat layer is created on each tube which is fixed to and integral with the tube proximate a second portion and the third portion of the outer surface and free from adherence to the tube proximate the first portion of the outer surface, wherein the overcoat layer on each tube includes a balloon portion which is the portion of the overcoat layer proximate the first portion of the outer surface which is free from adherence to the outer surface, the balloon portion of the overcoat layer and the first portion of the outer surface cooperating to define a balloon cavity which communicates with the first lumen via the first lumen access opening.

11. The method of claim 10 wherein step (a) includes extruding a continuous length of tubing, cutting the tubing into a plurality of tubes having uniform lengths, each of said tubes having an outer surface, first and second lumens, and distal and proximal ends, wherein step (a) further includes perforating the outer surface of each of tube to create the first lumen access opening and introducing a measured amount of a polymeric bonding composition into the first lumen such that a section of the first lumen between the first lumen access opening and the distal end of each tube is filled with said polymeric bonding composition, step (a) further including fixing a tip to the distal end of each tube such that access to the respective lumens via the distal end is restricted.

12. The method of claim 11 wherein, prior to step (b) and following step (a), said method further includes engaging said plurality of tubes upon a transportable support rack, said support rack including a plurality of support rods, each of said tubes being engaged upon one of said support rods; wherein steps (b) and (d) can be accomplished by transporting the plurality of tubes between a plurality of workstations in a prescribed sequence, wherein at least two of said workstations include tank means for holding a fluid material for coating said plurality of tubes simultaneously when said tubes are immersed in said fluid material.

13. The method of claim 12 wherein step (d) is followed by curing the overcoat layer, and securing an end piece to the proximal end of each of said tubes, wherein said end piece includes proximal openings communicating with the first and second lumens respectively, said steps of curing and securing being followed by introducing a fluid into the first lumen and the balloon cavity of each of the tubes, and withdrawing the fluid from the first lumen and the balloon cavity of each of the tubes and substantially removing the bond preventing agent therefrom.

14. A method of making a balloon catheter from a tube having an outer surface and a plurality of lumens, the tube having first and second lumens and distal and proximal ends, the outer surface including a first lumen access opening which communicates with the first lumen, the first lumen extending from the first opening to the proximal end of the tube, the distal end of the tube including a tip which prevents communication with the first and second lumens proximate the distal end of the tube, said method including the steps of:

(a) dipping the tube in a removable liquid bond preventing agent effective to form a coating on the outer surface of the tube such that areas of the outer surface which are coated with the removable bond preventing agent are generally inaccessible for the purpose of bonding therewith, wherein the removable bond preventing agent fills the first lumen access opening and at least a portion of the first lumen and coats first and third adjacent portions of the outer surface, said first lumen access opening being located in the first portion of the outer surface, wherein the step of dipping the tube in a removable liquid bond preventing agent includes filling a lower portion of the first lumen, wherein the removable liquid bond preventing agent is drawn into and retained within the lower portion of the first lumen by forces resulting at least in part from a capillary effect of the first lumen; and (b) subsequently dipping the tube in a polymeric bonding composition to form a resilient overcoat layer which bonds to a second portion and the third portion of the outer surface and coats the removable coating of bond preventing agent on the first portion of the outer surface; wherein the resilient overcoat layer is fixed to and integral with the tube proximate the second and third portions of the outer surface and is free from adherence to the tube proximate the first portion of the outer surface.

* * * * *

UNITED STATES PATENT AND TRADEMARK OFFICE
CERTIFICATE OF CORRECTION

PATENT NO. : 5,137,671

DATED : August 11, 1992

INVENTOR(S) : A. J. Conway et al.

It is certified that error appears in the above-identified patent and that said Letters Patent is hereby corrected as shown below:

In column 6, line 40, please change "solids" to --solid--

In column 6, line 61, please change "IN" to --In--.

In column 6, line 65, please change "of" to --a--.

In column 8, line 53, please change "accessing" to --access--.

Column 11, line 5, change "lower, palled 24 is advance" to --lowered, pallet 24 is advanced--

In column 11, line 6, please change "contain" to --containing--.

In column 13, line 25, after "coating" please insert --on--.

In column 13, line 32, after "coating" please insert --on--.

UNITED STATES PATENT AND TRADEMARK OFFICE
CERTIFICATE OF CORRECTION

PATENT NO. : 5,137,671

DATED : August 11, 1992

INVENTOR(S) : A. J. Conway et al

It is certified that error appears in the above-indentified patent and that said Letters Patent is hereby corrected as shown below:

Column 16, line 65, change "of tube" to --of the tubes--

Signed and Sealed this

Twenty-fourth Day of May, 1994

Attest:

BRUCE LEHMAN

*Attesting Officer*   *Commissioner of Patents and Trademarks*